United States Patent
Kim et al.

(10) Patent No.: US 10,307,069 B2
(45) Date of Patent: *Jun. 4, 2019

(54) BIO SIGNAL MEASURING APPARATUS USING BANDWIDTH OF PULSE SIGNAL AND USER MONITORING SYSTEM INCLUDING THE SAME

(71) Applicant: Industry-Academic Cooperation Foundation, Yonsei University, Seoul (KR)

(72) Inventors: Tae Wook Kim, Seoul (KR); Honggul Han, Busan (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 593 days.

This patent is subject to a terminal disclaimer.

(21) Appl. No.: 14/747,515

(22) Filed: Jun. 23, 2015

(65) Prior Publication Data

US 2015/0366470 A1   Dec. 24, 2015

(30) Foreign Application Priority Data

Jun. 23, 2014   (KR) .................. 10-2014-0076488

(51) Int. Cl.
| | | |
|---|---|---|
| *A61B 5/02* | (2006.01) | |
| *A61B 5/0245* | (2006.01) | |
| *A61B 5/024* | (2006.01) | |
| *A61B 5/05* | (2006.01) | |
| *A61B 5/00* | (2006.01) | |

(52) U.S. Cl.
CPC ........ *A61B 5/0245* (2013.01); *A61B 5/02444* (2013.01); *A61B 5/0507* (2013.01); *A61B 5/002* (2013.01); *A61B 5/0006* (2013.01)

(58) Field of Classification Search
CPC . A61B 5/0245; A61B 5/02444; A61B 5/0507; A61B 5/0006; A61B 5/002; A61B 5/6867; A61B 5/7278
See application file for complete search history.

(56) References Cited

FOREIGN PATENT DOCUMENTS

| | | |
|---|---|---|
| JP | H10-504976 | 5/1998 |
| JP | 2003-126090 | 5/2003 |
| JP | 2013-153783 A | 8/2013 |
| KR | 10-0233488 | 9/1999 |
| KR | 10-0665567 B1 | 12/2006 |
| KR | 10-2007-0120815 A | 12/2007 |
| KR | 10-2009-0022085 A | 3/2009 |

(Continued)

OTHER PUBLICATIONS

Takahiko et al—JP 2013153783 A, published Aug. 15, 2013, English translation provided.*

(Continued)

*Primary Examiner* — Mallika D Fairchild
(74) *Attorney, Agent, or Firm* — Sughrue Mion, PLLC

(57) ABSTRACT

A bio signal measuring apparatus is provided which a receiver configured to receive a pulse signal penetrating a person to be measured, a processing unit configured to process the pulse signal to analyze a bandwidth of the pulse signal and to measure a bio signal of the person to be measured based on an analysis result on the bandwidth, and a storage unit configured to store data used to measure the bio signal.

18 Claims, 9 Drawing Sheets

(56) References Cited

FOREIGN PATENT DOCUMENTS

| KR | 10-0905102 B1 | 6/2009 |
|----|---------------|--------|
| KR | 10-2011-0105411 A | 9/2011 |
| KR | 10-2013-0051992 | 5/2013 |
| KR | 10-2013-0124210 A | 11/2013 |
| KR | 10-2014-0073348 | 6/2014 |

OTHER PUBLICATIONS

Shin, J.Y., et al., A Study of Noncontact Heartbeat and Respiration Detection Using the Doppler Radar, The Institute of Electronics and Information Engineers, Jan. 2009, 9 pgs.

Wang, L., et al., 3-5 GHz 4-Channel UWB Beamforming Transmitter with 1° C. Scanning Resolution Through Calibrated Vernier Delay Line in 0.13-µm CMOS, IEEE Journal of Solid-State Circuits, 47(12), Dec. 2012, pp. 3145-3159.

Notice of Allowance for KR App No. 10-2014-0108129 dated Nov. 16, 2015, 5 pgs.

Notice of Allowance for KR App No. 10-2014-0076488 dated Nov. 16, 2015, 5 pgs.

\* cited by examiner

BIO SIGNAL MEASURING APPARATUS USING BANDWIDTH OF PULSE SIGNAL AND USER MONITORING SYSTEM INCLUDING THE SAME

CROSS-REFERENCE TO RELATED APPLICATIONS

A claim for priority under 35 U.S.C. § 119 is made to Korean Patent Application No. 10-2014-0076488 filed Jun. 23, 2014, in the Korean Intellectual Property Office, the entire contents of which are hereby incorporated by reference.

BACKGROUND

Embodiments of the inventive concepts described herein relate to an apparatus for measuring a bio signal apparatus using a bandwidth of a pulse signal and a user monitoring system including the same.

A method for measuring electrocardiogram (ECG) with electrodes contacting to a body of a person to be measured may be widely used to check a heart condition. However, the method for measuring the ECG using electrodes may be inconvenient to use because the electrodes are in contact with the body.

A non-contact type heartbeat measuring method may be used to solve inconvenience to measure a heartbeat in a contact type. In the non-contact type heartbeat measuring method, the heartbeat may be measured using a reflected wave that is reflected from a body of a person to be measured after transmitting a wireless signal toward a heart of the patient.

However, the method using the reflected wave may have a disadvantage in that an error due to movement of the person to be measured is great because the heartbeat is measured based on a distance between a transceiver and a body.

SUMMARY

Embodiments of the inventive concepts provide a bio signal measuring apparatus and a user monitoring system including the same, capable of measuring a bio signal including a heartbeat without influence due to movement of a person to be measured.

One aspect of embodiments of the inventive concept is directed to provide a bio signal measuring apparatus which includes a receiver configured to receive a pulse signal penetrating a person to be measured, a processing unit configured to process the pulse signal to analyze a bandwidth of the pulse signal and to measure a bio signal of the person to be measured based on an analysis result on the bandwidth, and a storage unit configured to store data used to measure the bio signal.

The pulse signal may be a signal where a pulse is repeated every predetermined pulse repetition period.

The receiver may include an antenna configured to receive a signal, an amplifier configured to amplify the received signal, a sampling unit configured to sample the amplified signal, and an analog-to-digital converter configured to convert the sampled signal to a digital signal.

The processing unit may analyze a bandwidth of a signal to measure a heartbeat of the person to be measured.

The processing unit may calculate a bandwidth of the pulse signal. The bandwidth is greater than a bandwidth threshold value, the processing unit may determine a period of a pulse signal having the bandwidth as a contraction period of a heart. The bandwidth is smaller than the bandwidth threshold value, the processing unit may determine a period of a pulse signal having the bandwidth as a distension period of a heart.

The processing unit may compare bandwidths before and after the pulse signal penetrates a person to be measured, to calculate a variation in the bandwidth. When the variation in the bandwidth is greater than a bandwidth variation threshold value, the processing unit may determine a period of a pulse signal having the variation as a contraction period of a heart; when the variation in the bandwidth is greater than the bandwidth variation threshold value, the processing unit may determine a period of a pulse signal having the variation as a distension period of a heart.

The processing unit may further analyze at least one of a center frequency or an amplitude of the pulse signal. The processing unit may measure a bio signal of the person to be measured, based on an analysis result about the bandwidth and an analysis result about at least one of the center frequency or the amplitude.

The processing unit may measure a heartbeat of the person to be measured by analyzing at least one of a bandwidth, a center frequency, and an amplitude of the pulse signal.

The processing unit may calculate the center frequency of the pulse signal. When the center frequency is greater than a center frequency threshold value, the processing unit may determine a period of pulse signal having the center frequency as a contraction period of a heart; when the center frequency is smaller than the center frequency threshold value, the processing unit may determine a period of pulse signal having the center frequency as a distension period of a heart.

The processing unit may compare center frequencies before and after the pulse signal penetrates a person to be measured, to calculate a variation in the center frequency. When the variation in the center frequency is smaller than a center frequency variation threshold value, the processing unit may determine a period of a pulse signal having the variation as a contraction period of a heart; when the variation in the center frequency is greater than the center frequency variation threshold value, the processing unit may determine a period of a pulse signal having the variation as a distension period of a heart.

The processing unit may calculate an amplitude of the pulse signal. When the amplitude is greater than an amplitude threshold value, the processing unit may determine a period of a pulse signal having the amplitude as a contraction period of a heart; when the amplitude is smaller than the amplitude threshold value, the processing unit may determine a period of a pulse signal having the amplitude as a distension period of a heart.

The processing unit may compare amplitudes before and after the pulse signal penetrates a person to be measured, to calculate a variation in the amplitude. When the variation in the amplitude is smaller than an amplitude variation threshold value, the processing unit may determine a period of a pulse signal having the variation as a contraction period of a heart; when the variation in the amplitude is smaller than the amplitude variation threshold value, the processing unit may determine a period of a pulse signal having the variation as a distension period of a heart.

The processing unit may convert the pulse signal from a time domain to a frequency domain to measure a bandwidth of the pulse signal in the frequency domain.

The processing unit may measure a duration of a pulse included in the pulse signal in the time domain and analyzes the bandwidth using the duration. When the duration is shorter than a duration threshold value corresponding to the bandwidth threshold value, the processing unit may determine a period of a pulse signal having the duration as a contraction period of a heart; when the duration is longer than the duration threshold value, the processing unit may determine a period of a pulse signal having the duration as a distension period of a heart.

The processing unit may measure a duration of a pulse included in the pulse signal in a time domain and compares durations before and after the pulse signal penetrates a person to be measured, to analyze a variation in the bandwidth using a variation in the duration. When the variation in the duration is smaller than a duration variation threshold value corresponding to the bandwidth variation threshold value, the processing unit may determine a period of a pulse signal having the variation as a contraction period of a heart; when the variation in the duration is greater than the duration variation threshold value, the processing unit may determine a period of a pulse signal having the variation as a distension period of a heart.

The processing unit may convert the pulse signal from a time domain to a frequency domain to measure a center frequency of the pulse signal in the frequency domain.

The processing unit may measure a time difference between positive and negative amplitudes of a pulse included in the pulse signal in a time domain and analyzes the center frequency using the time difference. When the time difference is smaller than a time difference threshold value corresponding to the center frequency threshold value, the processing unit may determine a period of a pulse signal having the time difference as a contraction period of a heart; when the time difference is greater than the time difference threshold value, the processing unit may determine a period of a pulse signal having the time difference as a distension period of a heart.

The processing unit may measure a time difference between positive and negative amplitude portions of a pulse included in the pulse signal in a time domain, may compare a time difference before the pulse signal penetrates a person to be measured with a time difference after the pulse signal penetrates a person to be measured to calculate a variation in the time difference, and may analyze a variation in the center frequency using a variation in the time difference. When the variation in the time difference is smaller than a time difference variation threshold value corresponding to the center frequency variation threshold value, the processing unit may determine a period of a pulse signal having the variation as a contraction period of a heart; when the variation in the time difference is greater than the time difference variation threshold value, the processing unit may determine a period of a pulse signal having the variation as a distension period of a heart.

A user monitoring system is provided which includes a transmitter configured to generate a pulse signal and transmit the pulse signal to a user, and a bio signal measuring apparatus facing the transmitter, with the user interposed between the transmitter and the bio signal measuring apparatus. The bio signal measuring apparatus includes a receiver configured to receive a pulse signal penetrating a person to be measured, a processing unit configured to process the pulse signal to analyze a bandwidth of the pulse signal and to measure a bio signal of the person to be measured based on an analysis result on the bandwidth, and a storage unit configured to store data used to measure the bio signal.

The processing unit may analyze a bandwidth of the pulse signal to measure a heartbeat of the user.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
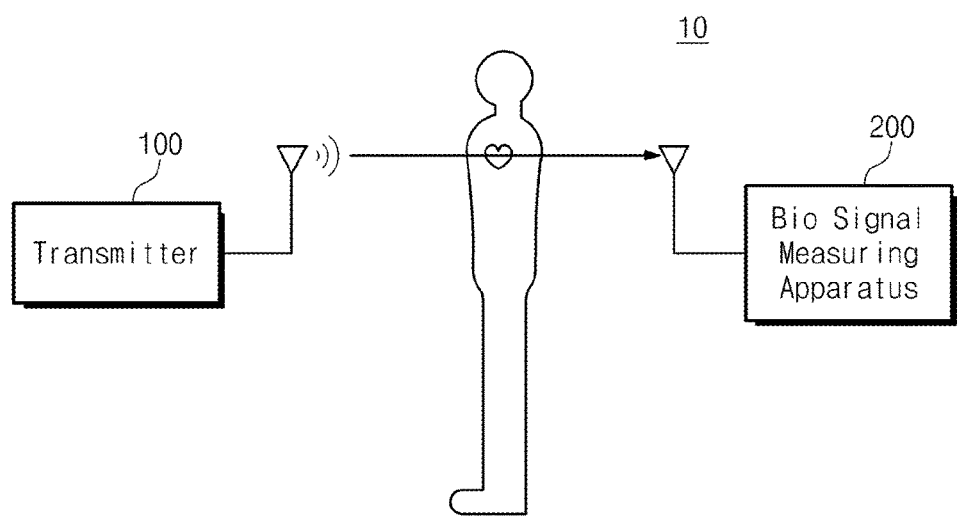
FIG. 1 is a block diagram schematically illustrating a user monitoring system according to an exemplary embodiment of the inventive concept.

Embodiments will be described in detail with reference to the accompanying drawings. The inventive concept, however, may be embodied in various different forms, and should not be construed as being limited only to the illustrated embodiments. Rather, these embodiments are provided as examples so that this disclosure will be thorough and complete, and will fully convey the concept of the inventive concept to those skilled in the art. Accordingly, known processes, elements, and techniques are not described with respect to some of the embodiments of the inventive concept. Unless otherwise noted, like reference numerals denote like elements throughout the attached drawings and written description, and thus descriptions will not be repeated. In the drawings, the sizes and relative sizes of layers and regions may be exaggerated for clarity.

It will be understood that, although the terms "first", "second", "third", etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the inventive concept.

Spatially relative terms, such as "beneath", "below", "lower", "under", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below. The device may be otherwise oriented (rotated 90 degrees or at other orientations) and the spatially relative descriptors used herein interpreted accordingly. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Also, the term "exemplary" is intended to refer to an example or illustration.

It will be understood that when an element or layer is referred to as being "on", "connected to", "coupled to", or "adjacent to" another element or layer, it can be directly on, connected, coupled, or adjacent to the other element or layer, or intervening elements or layers may be present. In contrast, when an element is referred to as being "directly on," "directly connected to", "directly coupled to", or "immediately adjacent to" another element or layer, there are no intervening elements or layers present.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

In the description below, it will be understood that when an element such as a layer, region, substrate, plate, or member is referred to as being "on" another element, it can be directly on the other element or intervening elements may be present. In contrast, the term "directly" means that there are no intervening elements.

FIG. 1 is a block diagram schematically illustrating a user monitoring system 10 according to an exemplary embodiment of the inventive concept.

As illustrated in FIG. 1, a user monitoring system 10 may contain a transmitter 100 and a bio signal measuring apparatus 200.

The transmitter 100 may generate a pulse signal and may transmit the pulse signal to a user. The bio signal measuring apparatus 200 may be disposed to face the transmitter 100 with the user interposed therebetween.

According to an exemplary embodiment of the inventive concept, the bio signal measuring apparatus 200 may measure a bio signal of the user using a pulse signal that is emitted from the transmitter 100 and penetrates the user.

According to an exemplary embodiment of the inventive concept, the bio signal measuring apparatus 200 may measure a heartbeat using the bio signal of the user, but the measured bio signal may not be limited thereto. As will be described later, as the pulse signal penetrates the user, signal characteristics including a bandwidth may vary. In this case, the bio signal measuring apparatus 200 may measure a condition or movement of an internal organ of the user as well as a heart.

The user monitoring system 10 may measure a bio signal of the user and may monitor a condition of the user based on the measured bio signal.

In exemplary embodiments, the user monitoring system 10 may be installed at a vehicle to monitor conditions of a passenger as well as a driver, but an application field of the user monitoring system 10 may not be limited thereto.

For example, the user monitoring system 10 may be installed at a place (e.g., a cinema or theater) where movement of a user is less, thereby monitoring a condition of the audience.

Figure 2:
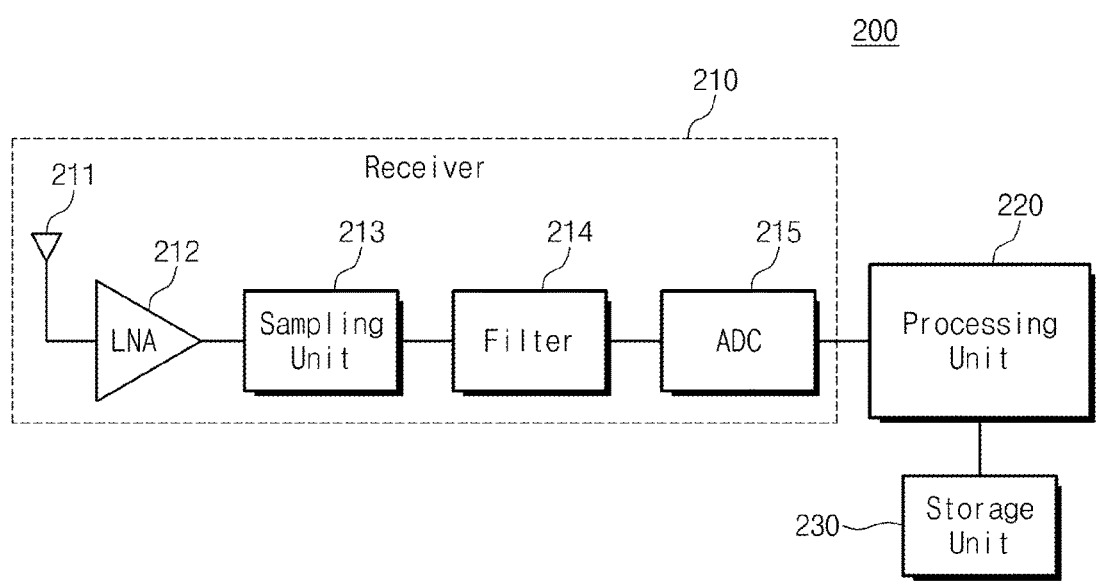
FIG. 2 is a block diagram schematically illustrating a bio signal measuring apparatus according to an exemplary embodiment of the inventive concept.

FIG. 2 is a block diagram schematically illustrating a bio signal measuring apparatus 200 according to an exemplary embodiment of the inventive concept.

As illustrated in FIG. 2, a bio signal measuring apparatus 200 may contain a receiver 210, a processing unit 220, and a storage unit 230.

The receiver 210 may receive a pulse signal that is emitted from a transmitter 100 and penetrates a person to be measured. The processing unit 220 may process the received pulse signal to analyze a bandwidth of the pulse signal and may measure a bio signal of the to-be-measured person based on a result of analyzing the bandwidth. The storage unit 230 may store data used to measure the bio signal.

In exemplary embodiments, the receiver 210 may contain an antenna 211, an amplifier 212, a sampling unit 213, and an analog-to-digital converter 215. The antenna 211 may receive a pulse signal that penetrates a user from which a bio signal is measured, that is, a person to be measured.

The amplifier 212 may amplify a received signal, and may be formed of, for example, a low noise amplifier. The sampling unit 213 may sample the amplified signal. The analog-to-digital converter 215 may convert the sampled signal into a digital signal. In exemplary embodiments, the a filter 214 may be further provided between the sampling unit 213 and the analog-to-digital converter 215 to remove unnecessary noise included in a signal at the sampling operation.

The processing unit 220 may process the digital signal to analyze a bandwidth of the pulse signal and may measure a bio signal of a to-be-measured person based on a result of analyzing the bio signal. The processing unit 220 may be a processor that calls and executes, the storage unit 230, a program used to measure a bio signal, and may include, for example, a central processing unit (CPU).

The storage unit 230 may be a storage device that stores a variety of data used to measure the bio signal and may include, for example, a register, a RAM, a ROM, a hard disk drive (HDD), a solid state drive (SSD), and the like.

Figure 3:
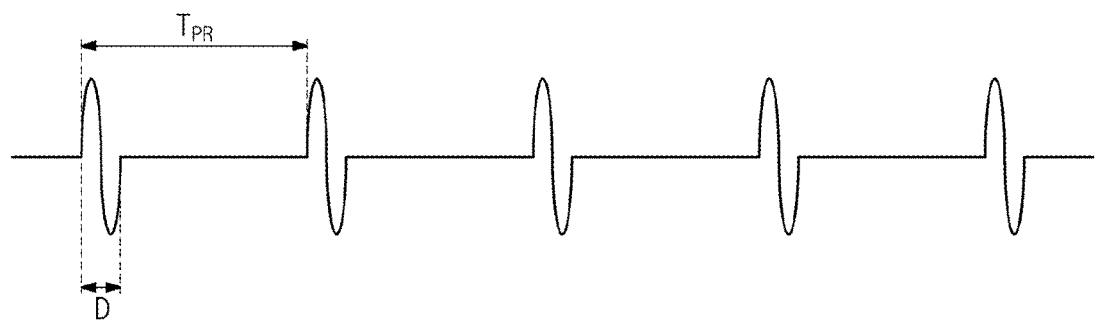
FIG. 3 is a diagram schematically illustrating a waveform of a time-domain pulse signal used to measure a bio signal of a to-be-measured person, according to an exemplary embodiment of the inventive concept.

FIG. 3 is a diagram schematically illustrating a waveform of a time-domain pulse signal used to measure a bio signal of a to-be-measured person, according to an exemplary embodiment of the inventive concept.

Referring to FIG. 3, a pulse signal may be a signal of which the pulse is iterated every pulse iteration period. In exemplary embodiments, the pulse may be an impulse having duration (D) corresponding to a nanosecond unit, and the pulse signal may be a ultra wide band (UWB) in which an impulse is repeated every pulse repetition period $T_{PR}$.

A pulse signal that is transmitted from a transmitter 100 and penetrates a to-be-measured person may be received by an antenna 211, and the received pulse signal may be amplified by an amplifier 212. The amplified pulse signal may be sampled by a sampling unit 213, and the sampled signal may be converted into a digital signal by an analog-to-digital converter 215.

A processing unit 220 may process the digital signal according to a predetermined process to analyze a bandwidth of the received pulse signal and may measure a bio signal of the to-be-measured person, for example, a heartbeat according to a result of analyzing the bandwidth.

Figure 4:
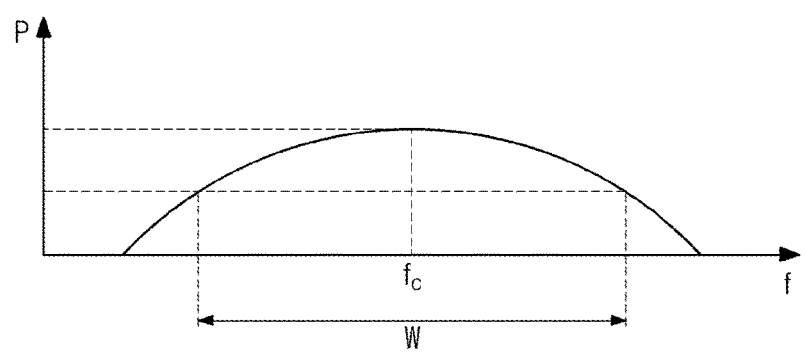
FIG. 4 is a diagram schematically illustrating power spectrum of a pulse signal used to measure a bio signal of a to-be-measured person, according to an exemplary embodiment of the inventive concept.

FIG. 4 is a diagram schematically illustrating power spectrum of a pulse signal used to measure a bio signal of a to-be-measured person, according to an exemplary embodiment of the inventive concept.

As described above, since a pulse signal used to measure a bio signal of a to-be-measured person is a signal in which an impulse having very short duration corresponding to a nanosecond unit is repeated, in a frequency domain, low power spectrum density may be distributed over a very wide bandwidth ranging to several gigahertzes as illustrated in FIG. 4.

According to an exemplary embodiment of the inventive concept, a bio signal such as a heartbeat may be measured by transmitting an ultra-wide band signal to a to-be-measured person and analyzing a bandwidth of a signal penetrating the to-be-measured person. Below, a process that a processing unit performs to measure a heartbeat of a bio signal will be more fully described with reference to accompanying drawings.

Figure 5:
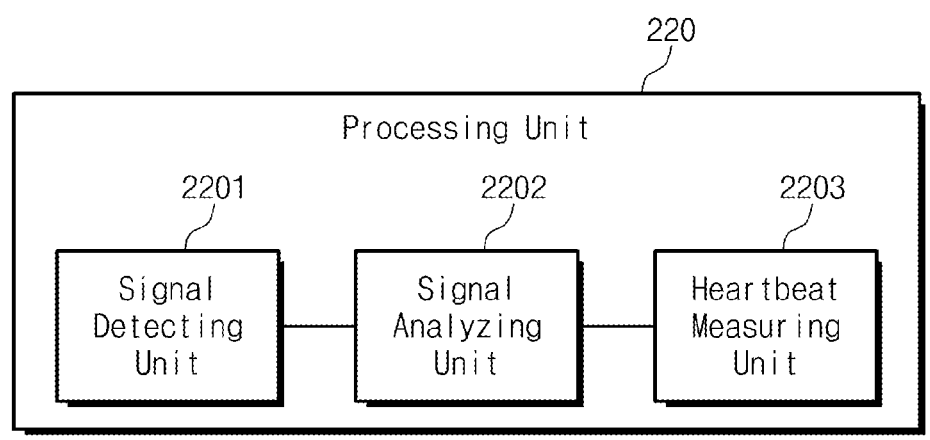
FIG. 5 is a block diagram schematically illustrating a processing unit according to an exemplary embodiment of the inventive concept.

FIG. 5 is a block diagram schematically illustrating a processing unit 220 according to an exemplary embodiment of the inventive concept.

As illustrated in FIG. 5, a processing unit 220 may contain a signal detecting unit 2201, a signal analyzing unit 2202, and a heartbeat measuring unit 2203.

The signal detecting unit 2201 may detect a signal, penetrating a heart of a to-be-measured person, from among a received pulse signal.

Even though a transmitter 100 transmits a pulse signal toward a heart of the to-be-measured person, a portion of the transmitted signal may penetrates an organ different from a heart, for example, a lung and reaches a bio signal measuring apparatus 200.

In this case, the signal detecting unit 2201 may merely detect a signal, penetrating a heart, from among the received pulse signal and may remove a signal penetrating a lung.

In exemplary embodiments, the signal detecting unit 2201 may detect a signal penetrating a heart using the strength of signal.

Since the heart is filled with liquid such as blood and the lung is filled with gas such as air, attenuation of a signal penetrating the heart may be different from that of a signal penetrating the lung.

Since attenuation of a signal penetrating gas is greater than that of a signal penetrating liquid, according to an exemplary embodiment of the inventive concept, the signal detecting unit 2201 may classify a received signal into two groups according to the strength of signal, and may determine a signal belonging to a group of which the strength is small, as a signal penetrating the heart.

In other exemplary embodiments, the signal detecting unit 2201 may detect a signal penetrating the heart using a time when a signal is received.

In detail, the signal detecting unit 2201 may determine a signal, first received, from among signals transmitted at the same time from a transmitter 100, as a signal penetrating a heart.

A signal that the bio signal measuring apparatus 200 first receives may correspond to a signal of which the transmission distance is shortest, and the signal may correspond to a signal that is transmitted in a straight line between a transmitter 100 and the bio signal measuring apparatus 200.

Accordingly, as illustrated in FIG. 1, in the case where the transmitter 100 and the bio signal measuring apparatus 200 are placed on a straight line passing through a heart of a person to be measured, the first received signal may be a signal passing through a heart.

The signal analyzing unit 2203 may analyze a bandwidth of a signal that the signal detecting unit 2201 detects as a signal penetrating a heart. The signal analyzing unit 2203 may measure a heartbeat of the to-be-measured person based on an analysis result of the signal analyzing unit 2202.

Figure 6:
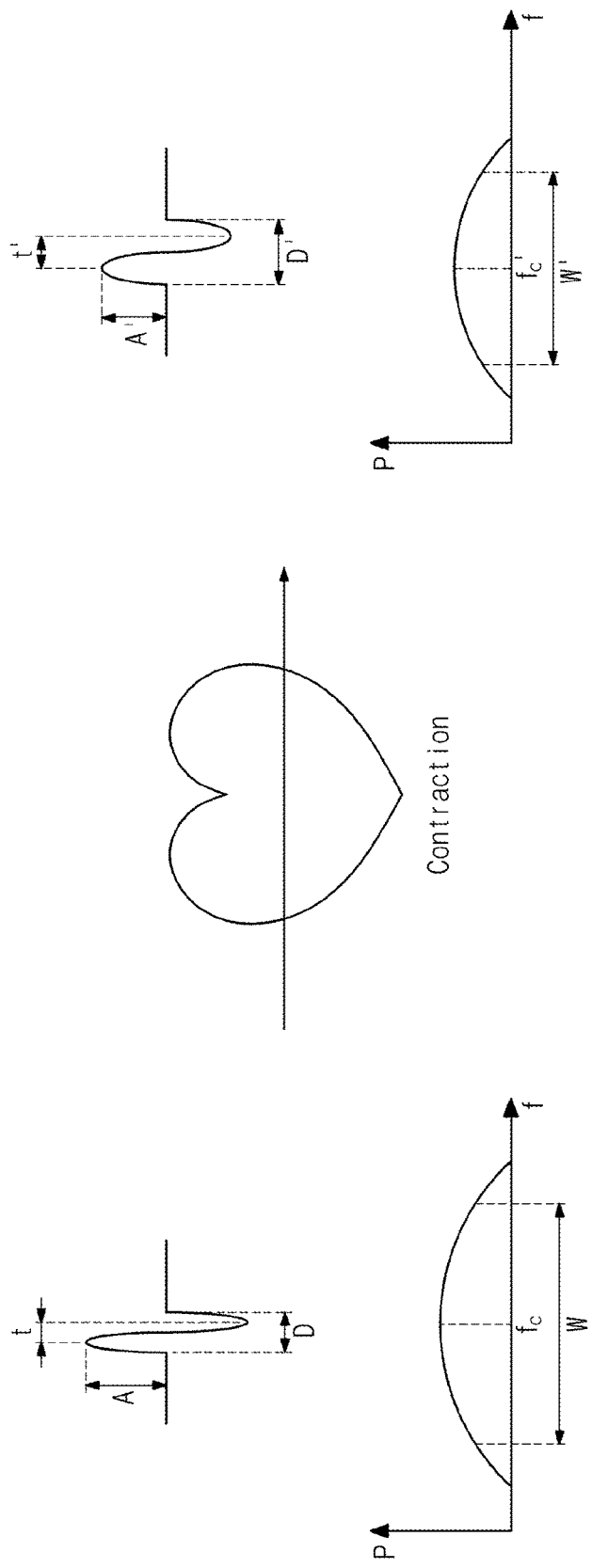
FIGS. 6 and 7 are diagrams schematically illustrating time-domain waveforms and frequency-domain power spectrums after a pulse signal passes through a contracted heart and a dilated heart, according to an exemplary embodiment of the inventive concept.
Figure 7:
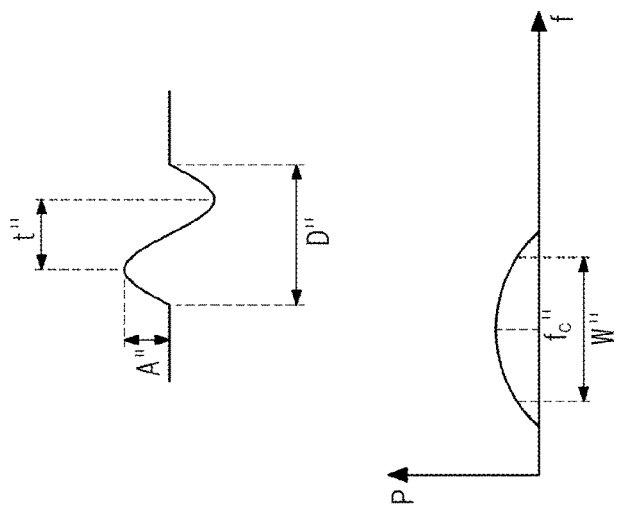
Figure 7:
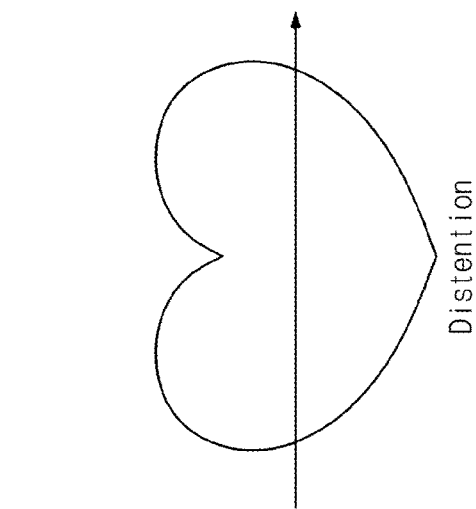
Figure 7:
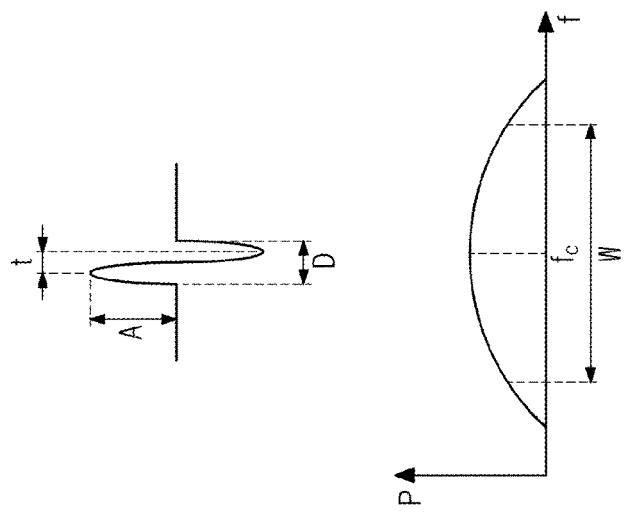

FIGS. 6 and 7 are diagrams schematically illustrating time-domain waveforms and frequency-domain power spectrums after a pulse signal passes through a contracted heart and a dilated heart, according to an exemplary embodiment of the inventive concept.

According to an exemplary embodiment of the inventive concept, in the case where a pulse signal penetrates a heart, a center frequency fc and amplitude A as well as a bandwidth W may decrease, and the decrement may vary according to the size of heart.

For example, as illustrated in FIGS. 6 and 7, it may be assumed that a pulse signal transmitted toward a heart of a to-be-measured person has amplitude A in a time domain and a center frequency fc and a bandwidth W in a frequency domain. Furthermore, it may be assumed that when the size of the heart is reduced due to contraction, the pulse signal transmitted toward the heart has amplitude A' in a time domain and a center frequency fc' and a bandwidth W' in a frequency domain. Furthermore, it may be assumed that when the size of the heart is reduced due to distention, the pulse signal transmitted toward the heart has amplitude A" in a time domain and a center frequency fc" and a bandwidth W" in a frequency domain. According to such assumptions, an amplitude relation between signals may be A>A'>A", a center frequency relation between the signals may be fc>fc'>fc", and a bandwidth relation between the signals may be W>W'>W".

That is, according to an exemplary embodiment of the inventive concept, as the size of heart becomes larger, a center frequency fc of a pulse signal penetrating a heart may become lower, its bandwidth W may become narrower, and its amplitude A may become smaller.

According to an exemplary embodiment of the inventive concept, a processing unit 220 may measure a heartbeat by monitoring a bandwidth W, a center frequency fc, and amplitude A of a received pulse signal to detect contraction and distention of the heart.

In other exemplary embodiments, the processing unit 220 may measure a heartbeat by monitoring variations in a bandwidth W, a center frequency fc, and amplitude A of a received pulse signal to detect contraction and distention of the heart.

Below, an operation in which the processing unit 220 measures a heartbeat using a pulse signal will be more fully described with reference to accompanying drawings.

Figure 8:
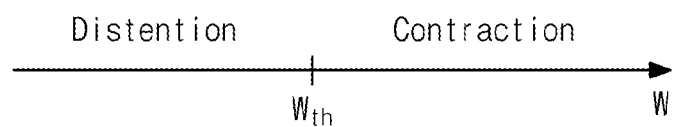
FIG. 8 is a diagram for describing a method for measuring a heartbeat using a bandwidth of a pulse signal, according to an exemplary embodiment of the inventive concept.

FIG. 8 is a diagram for describing a method for measuring a heartbeat using a bandwidth W of a pulse signal, according to an exemplary embodiment of the inventive concept.

According to an exemplary embodiment of the inventive concept, after calculating a bandwidth W of a pulse signal, a processing unit 220 may compare the bandwidth W with a predetermined threshold value to determine whether a heart is contracted or distended.

In detail, referring to FIG. 8, the processing unit 220 may calculate a bandwidth W of the pulse signal. When the bandwidth W is greater than a predetermined bandwidth threshold value $W_{th}$, the processing unit 220 may determine a period of a pulse signal having the bandwidth, as a contraction period of a heart. When the bandwidth W is smaller than the predetermined bandwidth threshold value $W_{th}$, the processing unit 220 may determine a period of a pulse signal having the bandwidth, as a distention period of a heart.

In other words, the processing unit 220 may determine, as a contraction period of a heart, a period where a bandwidth W of a received pulse signal is greater than a predetermined level and may determine, as a distention period of a heart, a period where the bandwidth W of the received pulse signal is smaller than the predetermined level.

Figure 9:
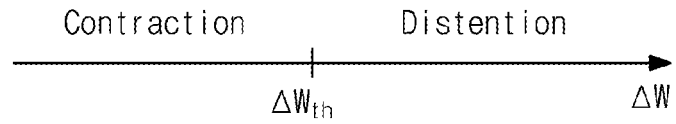
FIG. 9 is a diagram for describing a method for measuring a heartbeat using variations in bandwidth before and after a pulse signal penetrates a heart, according to an exemplary embodiment of the inventive concept.

FIG. 9 is a diagram for describing a method for measuring a heartbeat using variations ΔW in bandwidth before and after a pulse signal penetrates a heart, according to an exemplary embodiment of the inventive concept.

In exemplary embodiments, a processing unit 220 may compare bandwidths W before and after a pulse signal passes through a heart, to calculate a variation ΔW in bandwidth. The processing unit 220 may compare the variation ΔW with a predetermined threshold value to determine whether the heart is contracted or distended.

In detail, the processing unit 220 may compare a bandwidth before the pulse signal penetrates a to-be-measured person and a bandwidth after the pulse signal penetrates the to-be-measured person, to calculate the variation ΔW in bandwidth W before and after the pulse signal penetrates the to-be-measured person. When the variation ΔW in bandwidth is smaller than a predetermined bandwidth variation threshold value $ΔW_{th}$, a period of the pulse signal having such variation ΔW may be determined as a contraction period of a heart. When the variation ΔW in bandwidth is greater than the bandwidth variation threshold value $ΔW_{th}$, a period of the pulse signal having such variation ΔW may be determined as a distention period of a heart.

In other words, the processing unit 220 may determine, as a contraction period of a heart, a period where the variation ΔW in bandwidth before and after the pulse signal penetrates the to-be-measured person is smaller than a predetermined level, and may determine, as a distention period, a period where the variation ΔW in bandwidth is greater than the predetermined level.

A heart filled with blood may have a characteristic of a low pass filter. For this reason, as the size of heart becomes larger, a bandwidth of a pulse signal passing through the heart may become narrower. According to an exemplary embodiment of the inventive concept, a heartbeat of a user may be measured using a bandwidth related characteristic.

In addition, according to another exemplary embodiment of the inventive concept, the processing unit 220 may further analyze at least one of a center frequency fc or amplitude A of a pulse signal and may measure a bio signal of a to-be-measured person, based on an analysis result about the bandwidth W and an analysis result about at least one of the center frequency fc or the amplitude A.

Figure 10:
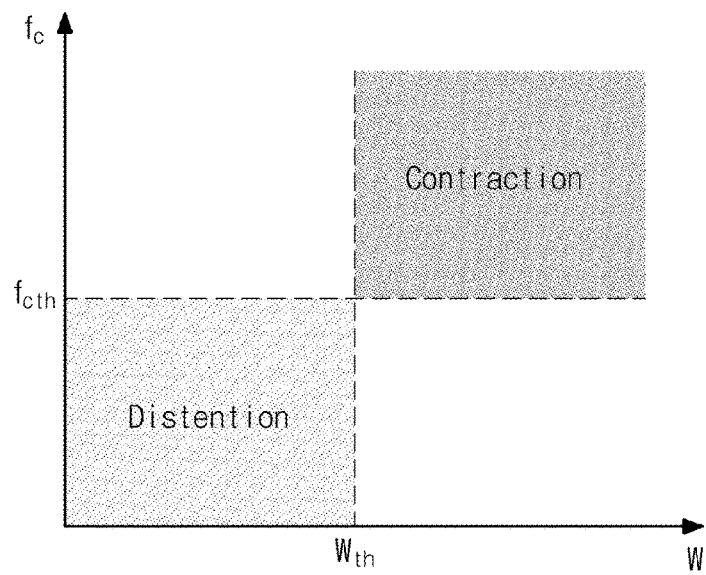
FIG. 10 is a diagram for describing a method for measuring a heartbeat using a bandwidth and a center frequency of a pulse signal, according to an exemplary embodiment of the inventive concept.

FIG. 10 is a diagram for describing a method for measuring a heartbeat using a bandwidth W and a center frequency fc of a pulse signal, according to an exemplary embodiment of the inventive concept.

In exemplary embodiments, a processing unit 220 may further analyze a center frequency fc of a pulse signal as well as a bandwidth W thereof and may determine whether a heart is contracted or distended, based on the analysis result.

In detail, the processing unit 220 may calculate the center frequency fc of a pulse signal. When the center frequency fc is higher than a predetermined center frequency threshold value $f_{cth}$, the processing unit 220 may determine, as a distention period of a heart, a period where a pulse signal has the center frequency fc. When the center frequency fc is lower than the center frequency threshold value $f_{cth}$, the processing unit 220 may determine, as a contraction period of a heart, a period where a pulse signal has the center frequency fc.

In exemplary embodiments, the processing unit 220 may more accurately determine whether a heart is contracted or distended, by measuring a heartbeat using a center frequency fc of a received pulse signal as well as a bandwidth W thereof.

For example, as illustrated in FIG. 10, the processing unit 220 may determine, a contraction period of a heart, a period where a bandwidth W of a pulse signal is greater than a bandwidth threshold value $W_{th}$ and a center frequency fc is higher than a center frequency threshold value $f_{cth}$. In contrast, the processing unit 220 may determine, a distension period of a heart, a period where a bandwidth W of a pulse signal is smaller than the bandwidth threshold value $W_{th}$ and a center frequency fc is lower than the center frequency threshold value $f_{cth}$.

As such, conditions used to determine whether a heart is contracted or distended may increase, thereby reducing an error occurring in measuring a heartbeat and measuring a heartbeat more accurately.

In exemplary embodiments, the processing unit 220 may grade a score based on a difference between a bandwidth W of a received pulse signal and a bandwidth threshold value $W_{th}$ and may grade a score based on a difference between a center frequency fc of the received pulse signal and a center frequency threshold value $f_{cth}$. Next, the processing unit 220 may assign the same or different weights to the score about the bandwidth W and the score about the center frequency fc and may determine whether a heart is contrasted or distended, using a final score obtained by adding the weighted scores. In this case, the reliability of measurement may be enhanced by assigning a greater weight to one, important to measure a heartbeat, from among the bandwidth W and the center frequency fc.

Figure 11:
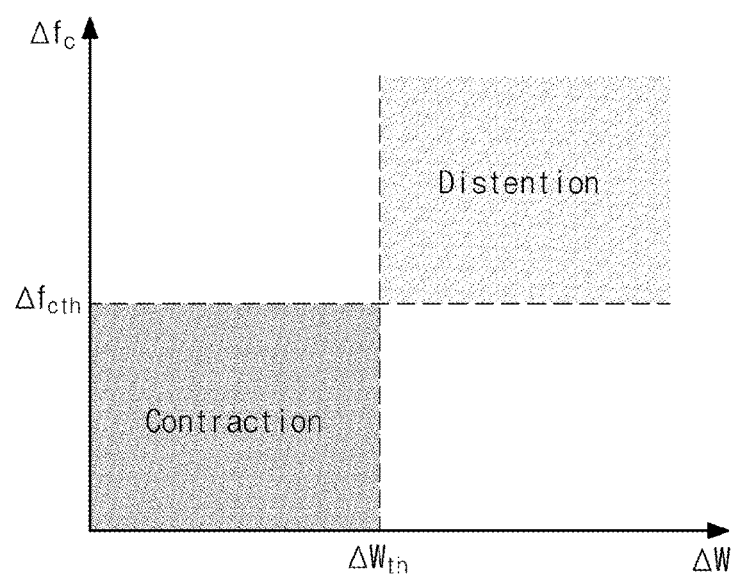
FIG. 11 is a diagram for describing a method for measuring a heartbeat using a bandwidth variation and a center frequency variation of a pulse signal, according to another exemplary embodiment of the inventive concept.

FIG. 11 is a diagram for describing a method for measuring a heartbeat using a bandwidth variation ΔW and a center frequency variation Δfc of a pulse signal, according to another exemplary embodiment of the inventive concept.

In exemplary embodiments, a processing unit 220 may further analyze a center frequency variation Δfc of a pulse signal as well as a bandwidth variation ΔW thereof and may determine whether a heart is contrasted or distended, based on the analysis result.

In detail, the processing unit 220 may compare center frequencies before and after a pulse signal passes through a to-be-measured person, to calculate a center frequency variation Δfc before and after the pulse signal passes through the to-be-measured person. When the variation Δfc in the center frequency is smaller than a predetermined center frequency variation threshold value $\Delta f_{cth}$, the processing unit 220 may determine, as a contraction period of a heart, a period where the pulse signal has the variation. When the variation Δfc in the center frequency is greater than the center frequency variation threshold value $\Delta f_{cth}$, the processing unit 220 may determine, as a distension period of a heart, a period where the pulse signal has the variation.

In exemplary embodiments, the processing unit 220 may more accurately determine whether a heart is contracted or distended, by measuring a heartbeat using a center frequency variation Δfc of a received pulse signal as well as a bandwidth variation ΔW thereof.

For example, as illustrated in FIG. 11, the processing unit 220 may determine, as a contraction period of a heart, a period where a bandwidth variation ΔW of a pulse signal is smaller than a bandwidth variation threshold value $\Delta W_{th}$ and a center frequency variation Δfc is smaller than a center frequency variation threshold value $\Delta f_{cth}$. In contrast, the processing unit 220 may determine, as a distension period of a heart, a period where the bandwidth variation ΔW of the pulse signal is greater than the bandwidth variation threshold value $\Delta W_{th}$ and the center frequency variation Δfc is greater than the center frequency variation threshold value $\Delta f_{cth}$.

In exemplary embodiments, the processing unit 220 may grade a score based on a difference between a bandwidth variation ΔW of a received pulse signal and a bandwidth variation threshold value $\Delta W_{th}$ and may grade a score based on a difference between a center frequency variation Δfc of the received pulse signal and a center frequency variation threshold value $\Delta f_{cth}$. Next, the processing unit 220 may assign the same or different weights to the score about the bandwidth variation ΔW and the score about the center frequency variation Δfc and may determine whether a heart is contrasted or distended, using a final score obtained by adding the weighted scores. In this case, the reliability of measurement may be enhanced by assigning a greater weight to one, important to measure a heartbeat, from among the bandwidth variation ΔW and the center frequency variation Δfc.

Figure 12:
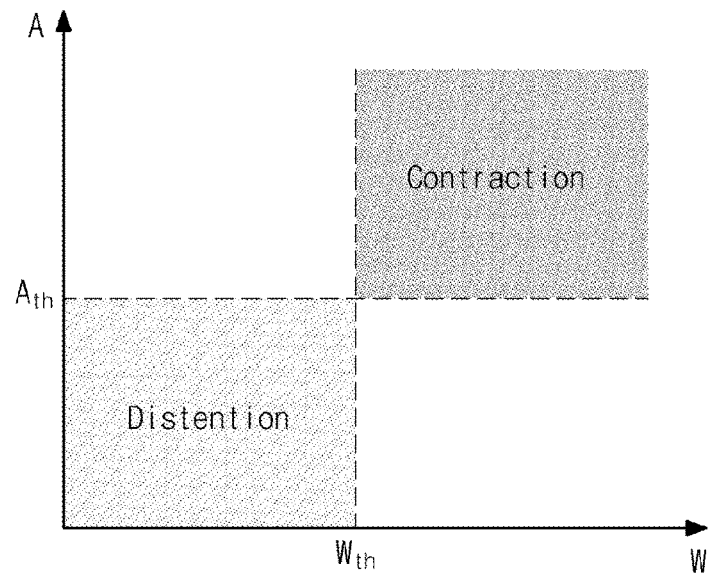
FIG. 12 is a diagram for describing a method for measuring a heartbeat using a bandwidth and amplitude of a pulse signal, according to still another exemplary embodiment of the inventive concept.

FIG. 12 is a diagram for describing a method for measuring a heartbeat using a bandwidth W and amplitude A of a pulse signal, according to still another exemplary embodiment of the inventive concept.

In exemplary embodiments, a processing unit 220 may further analyze amplitude A of a pulse signal as well as a bandwidth W thereof and may determine whether a heart is contrasted or distended, based on the analysis result.

In detail, the processing unit 220 may calculate amplitude A of the pulse signal. When the amplitude A is greater than a predetermined amplitude threshold value $A_{th}$, the processing unit 220 may determine, as a contraction period of a heart, a period where the pulse signal has the amplitude. When the amplitude A is smaller than the amplitude threshold value $A_{th}$, the processing unit 220 may determine, as a distension period of a heart, a period where the pulse signal has the amplitude.

In exemplary embodiments, the processing unit 220 may more accurately determine whether a heart is contracted or distended, by measuring a heartbeat using amplitude A of a received pulse signal as well as a bandwidth W thereof.

For example, as illustrated in FIG. 12, the processing unit 220 may determine, as a contraction period of a heart, a period where a bandwidth W of a pulse signal is greater than a bandwidth threshold value $W_{th}$ and amplitude A is greater than an amplitude threshold value $A_{th}$. In contrast, the processing unit 220 may determine, as a distension period of a heart, a period where the bandwidth W of the pulse signal is smaller than the bandwidth threshold value $W_{th}$ and the amplitude A is smaller than the amplitude threshold value $A_{th}$.

In exemplary embodiments, the processing unit 220 may grade a score based on a difference between a bandwidth W of a received pulse signal and a bandwidth threshold value $W_{th}$ and may grade a score based on a difference between amplitude A of the received pulse signal and an amplitude threshold value $A_{th}$. Next, the processing unit 220 may assign the same or different weights to the score about the bandwidth W and the score about the amplitude A and may determine whether a heart is contrasted or distended, using a final score obtained by adding the weighted scores. In this case, the reliability of measurement may be enhanced by assigning a greater weight to one, important to measure a heartbeat, from among the bandwidth W and the amplitude A.

Figure 13:
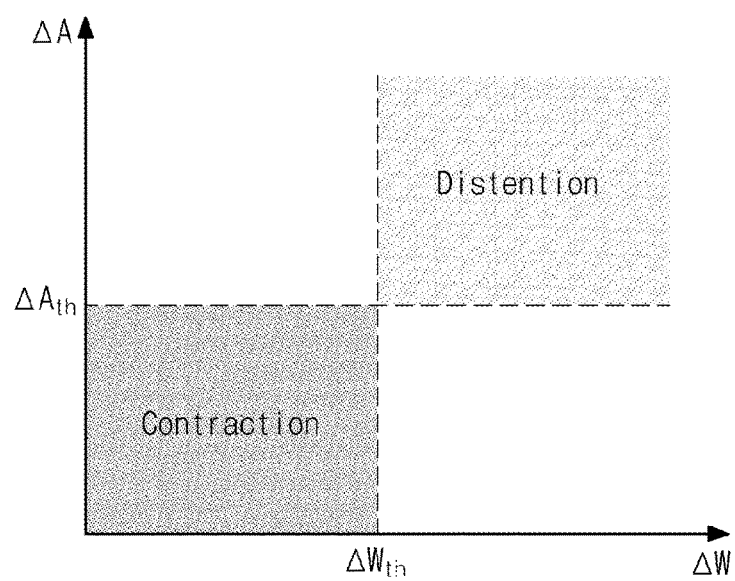
FIG. 13 is a diagram for describing a method for measuring a heartbeat using a bandwidth variation and an amplitude variation of a pulse signal, according to still another exemplary embodiment of the inventive concept.

FIG. 13 is a diagram for describing a method for measuring a heartbeat using a bandwidth variation ΔW and an amplitude variation ΔA of a pulse signal, according to still another exemplary embodiment of the inventive concept.

In exemplary embodiments, a processing unit 220 may further analyze an amplitude variation ΔA of a pulse signal as well as a bandwidth variation ΔW thereof and may determine whether a heart is contrasted or distended, based on the analysis result.

In detail, the processing unit 220 may compare amplitudes of a pulse signal before and after the pulse signal passes through a heart of a to-be-measured person, to calculate an amplitude variation ΔA. When the amplitude variation ΔA is smaller than a predetermined amplitude variation threshold value $\Delta A_{th}$, the processing unit 220 may determine, as a contraction period of a heart, a period where the pulse signal has the amplitude variation ΔA. When the amplitude variation ΔA is greater than the amplitude variation threshold value $\Delta A_{th}$, the processing unit 220 may determine, as a distension period of a heart, a period where the pulse signal has the amplitude variation ΔA.

In exemplary embodiments, the processing unit 220 may more accurately determine whether a heart is contracted or distended, by measuring a heartbeat using an amplitude variation ΔA of a received pulse signal as well as a bandwidth variation ΔW thereof.

For example, as illustrated in FIG. 13, the processing unit 220 may determine, as a contraction period of a heart, a period where a bandwidth variation ΔW of a pulse signal is smaller than a bandwidth variation threshold value $\Delta W_{th}$ and an amplitude variation ΔA is smaller than an amplitude variation threshold value $\Delta A_{th}$. In contrast, the processing unit 220 may determine, as a distension period of a heart, a period where the bandwidth variation ΔW of the pulse signal is greater than the bandwidth variation threshold value $\Delta W_{th}$ and the amplitude variation ΔA is greater than the amplitude variation threshold value $\Delta A_{th}$.

In exemplary embodiments, the processing unit 220 may grade a score based on a difference between a bandwidth variation ΔW of a received pulse signal and a bandwidth variation threshold value $\Delta W_{th}$ and may grade a score based on a difference between an amplitude variation ΔA of the received pulse signal and an amplitude variation threshold value $\Delta A_{th}$. Next, the processing unit 220 may assign the same or different weights to the score about the bandwidth variation ΔW and the score about the amplitude variation ΔA and may determine whether a heart is contrasted or distended, using a final score obtained by adding the weighted scores. In this case, the reliability of measurement may be enhanced by assigning a greater weight to one, important to measure a heartbeat, from among the bandwidth variation ΔW and the amplitude variation ΔA.

Embodiments of the inventive concept may be illustrated as a heartbeat is measured using a result of analyzing a center frequency fc or amplitude A of a pulse signal as well as a result of analyzing a bandwidth W thereof or a result of analyzing a center frequency variation Δfc or an amplitude variation ΔA as well as a result of analyzing a bandwidth variation ΔW. However, the scope and spirit of the inventive concept may not be limited thereto. For example, a heartbeat may be measured using a bandwidth W, a center frequency fc, and amplitude A, using a bandwidth variation ΔW, a center frequency variation Δfc, and an amplitude variation ΔA, or using a combination of two or more of the bandwidth W, the center frequency fc, the amplitude A, the bandwidth variation ΔW, the center frequency variation Δfc, and the amplitude variation ΔA.

According to an exemplary embodiment of the inventive concept, the processing unit 220 may convert a received pulse signal from a time domain to a frequency domain and may measure a center frequency or a bandwidth of a pulse signal in the time domain. At this time, the processing unit 220 may obtain a frequency spectrum of pulse signal using a Fourier transform algorithm. However, the scope and spirit of the inventive concept may not be limited thereto.

According to another exemplary embodiment of the inventive concept, the processing unit may process a received pulse signal in a time domain without converting into a frequency domain to analyze a bandwidth or a center frequency.

In exemplary embodiments, the processing unit 220 may measure duration D of a pulse included in a pulse signal in a time domain and may analyze a bandwidth W of a pulse signal using the duration D.

Figure 14:
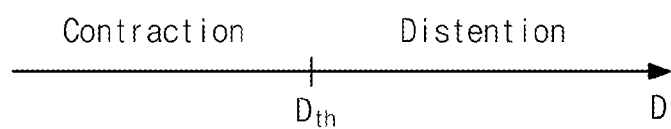
FIG. 14 is a diagram for describing a method for measuring a heartbeat by analyzing a bandwidth using duration of a pulse signal, according to still another exemplary embodiment of the inventive concept.

FIG. 14 is a diagram for describing a method for measuring a heartbeat by analyzing a bandwidth W using duration D of a pulse signal, according to still another exemplary embodiment of the inventive concept.

For example, referring to FIG. 14, a processing unit 220 may compare duration D with a duration threshold value $D_{th}$ corresponding to the above-described bandwidth threshold value $W_{th}$. When the duration D is shorter than the bandwidth threshold value $W_{th}$, a period where a pulse signal has the duration may be determined as a contraction period of a heart. When the duration D is longer than the bandwidth threshold value $W_{th}$, a period where a pulse signal has the duration may be determined as a distension period of a heart.

Furthermore, the processing unit 220 may measure duration D of a pulse included in a pulse signal in a time domain and may compare durations before and after the pulse signal passes through a to-be-measured person, to calculate a duration variation ΔD before and after the pulse signal passes through a to-be-measured person. Next, the processing unit 220 may analyze a bandwidth variation ΔW using the duration variation ΔD.

For example, the processing unit 220 may compare the duration variation ΔD with a duration variation threshold value ΔDth corresponding to the bandwidth variation threshold value $\Delta W_{th}$. When the duration variation ΔD is smaller than the duration variation threshold value ΔDth, the processing unit 220 may determine, as a contraction period of a heart, a period where a pulse signal has the duration variation ΔD. When the duration variation ΔD is greater than the duration variation threshold value ΔDth, the processing unit 220 may determine, as a distension period of a heart, a period where a pulse signal has the duration variation ΔD.

Furthermore, the processing unit 220 may analyze not only a bandwidth W based on duration D of a pulse signal, but it may analyze a center frequency fc based on a time difference t (in FIGS. 6 and 7) between a pulse portion having positive amplitude and pulse portion having negative amplitude.

Figure 15:
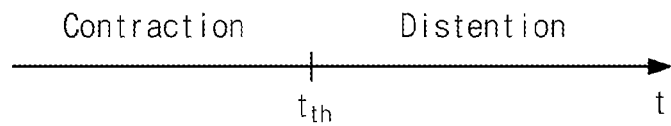
FIG. 15 is a diagram for describing a method for measuring a heartbeat by analyzing a center frequency using a time difference t between a pulse portion having positive amplitude and a pulse portion having negative amplitude, according to a further exemplary embodiment of the inventive concept.

FIG. 15 is a diagram for describing a method for measuring a heartbeat by analyzing a center frequency fc using a time difference t between a pulse portion having positive amplitude and a pulse portion having negative amplitude, according to a further exemplary embodiment of the inventive concept.

For example, referring to FIG. 15, a processing unit 220 may measure a time difference t of a pulse signal in a time domain and may compare the measured time difference t with a time difference threshold value $t_{th}$ corresponding to the above-described center frequency threshold value $f_{cth}$. When the time difference t is smaller than the time difference threshold value $t_{th}$, the processing unit 220 may determine, as a contraction period of a heart, a period where the pulse signal has the time difference t. When the time difference t is greater than the time difference threshold value $t_{th}$, the processing unit 220 may determine, as a distension period of a heart, a period where the pulse signal has the time difference t.

Also, the processing unit 220 may measure the time difference t in the time domain and may calculate a time difference variation Δt by comparing time differences before and after the pulse signal penetrates a person to be measured. The processing unit 220 may analyze a variation Δfc in a center frequency fc using the variation Δt in the time difference.

For example, the processing unit 220 may compare the time difference variation Δt with a time difference variation threshold value $\Delta t_{th}$ corresponding to the above-described center frequency variation threshold value $\Delta f_{cth}$. When the time difference variation Δt is smaller than the time difference variation threshold value $\Delta t_{th}$, the processing unit 220 may determine, as a contraction period of a heart, a period where the pulse signal has the time difference variation $\Delta t$. When the time difference variation $\Delta t$ is greater than the time difference variation threshold value $\Delta t_{th}$, the processing unit 220 may determine, as a distension period of a heart, a period where the pulse signal has the time difference variation $\Delta t$.

As such, a heartbeat may be measured by directly measuring duration D or a time difference t in a time domain, not converting a received pulse signal into a frequency-domain signal to measure a bandwidth W or a center frequency fc, thereby processing a signal more simply and making it easy to implement a system.

A bio signal measuring apparatus and a user monitoring system according to an exemplary embodiment of the inventive concept may perform measurement of a bio signal of a user including a heartbeat and monitoring of a user condition, using a bandwidth of a pulse signal penetrating a body of the user. Accordingly, a bio signal may be accurately measured without influence of movement of the user.

Furthermore, it may be possible to improve accuracy of measurement using a wide bandwidth in measuring bio signal by using an impulse signal of which the duration is short. Also, the embodiment of the inventive concept may remove an error due to motion of a body using a wave reflected from a body of a to-be-measured person as well as a penetrated wave. It may be possible to reduce influence of fading using a difference between arrival times of signals received through multiple paths.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A bio signal measuring apparatus comprising:
a receiver configured to receive a pulse signal penetrating a person to be measured;
a processing unit configured to detect a pulse signal of a heart of the person from the received pulse signal, process the pulse signal of the heart to analyze a bandwidth of the pulse signal of the heart and to measure a bio signal of the person to be measured based on an analysis result on the bandwidth, wherein the pulse signal of the heart of the person is a pulse signal having penetrated through the heart of the person among the received pulse signal; and
a storage unit configured to store data used to measure the bio signal,
wherein the processing unit analyzes the bandwidth of the pulse signal of the heart, measures a heartbeat of the person to be measured according to an analysis result of the bandwidth and monitors a condition of the person based on the measured heartbeat of the person,
wherein the processing unit calculates the bandwidth of the pulse signal of the heart,
wherein when the bandwidth is greater than a bandwidth threshold value, the processing unit determines a period of the pulse signal having the bandwidth as a contraction period of the heart, and
wherein when the bandwidth is smaller than the bandwidth threshold value, the processing unit determines a period of the pulse signal of the heart having the bandwidth as a distension period of the heart.

2. The bio signal measuring apparatus of claim 1, wherein the pulse signal of the heart is a signal where a pulse is repeated every predetermined pulse repetition period.

3. The bio signal measuring apparatus of claim 1, wherein the receiver comprises:
an antenna configured to receive the pulse signal;
an amplifier configured to amplify the received pulse signal;
a sampling unit configured to sample the amplified pulse signal; and
an analog-to-digital converter configured to convert the sampled pulse signal to a digital signal.

4. The bio signal measuring apparatus of claim 1, wherein the processing unit compares bandwidths before and after the pulse signal penetrates the heart of the person to be measured, to calculate a variation in the bandwidth,
wherein when the variation in the bandwidth is greater than a bandwidth variation threshold value, the processing unit determines a period of the pulse signal of the heart having the variation as a contraction period of the heart, and
wherein when the variation in the bandwidth is greater than the bandwidth variation threshold value, the processing unit determines a period of the pulse signal of the heart having the variation as a distension period of the heart.

5. The bio signal measuring apparatus of claim 4, wherein the processing unit measures a duration of a pulse included in the pulse signal of the heart in a time domain and compares durations before and after the pulse signal penetrates the heart of the person to be measured, to analyze a variation in the bandwidth using a variation in the duration,
wherein when the variation in the duration is smaller than a duration variation threshold value corresponding to the bandwidth variation threshold value, the processing unit determines a period of the pulse signal of the heart having the variation as a contraction period of the heart, and
wherein when the variation in the duration is greater than the duration variation threshold value, the processing unit determines a period of the pulse signal of the heart having the variation as a distension period of the heart.

6. The bio signal measuring apparatus of claim 1, wherein the processing unit further analyzes at least one of a center frequency or an amplitude of the pulse signal of the heart, and
wherein the processing unit measures the bio signal of the person to be measured, based on an analysis result about the bandwidth and an analysis result about at least one of the center frequency or the amplitude.

7. The bio signal measuring apparatus of claim 6, wherein the processing unit converts the pulse signal of the heart from a time domain to a frequency domain to measure a center frequency of the pulse signal of the heart in the frequency domain.

8. The bio signal measuring apparatus of claim 6, wherein the processing unit measures the heartbeat of the person to be measured by analyzing at least one of a bandwidth, a center frequency, and an amplitude of the pulse signal of the heart.

9. The bio signal measuring apparatus of claim 8, wherein the processing unit calculates the center frequency of the pulse signal of the heart,
wherein when the center frequency is greater than a center frequency threshold value, the processing unit determines a period of the pulse signal of the heart having the center frequency as a contraction period of the heart, and wherein when the center frequency is smaller than the center frequency threshold value, the processing unit determines a period of the pulse signal of the heart having the center frequency as a distension period of the heart.

10. The bio signal measuring apparatus of claim 9, wherein the processing unit measures a time difference between positive and negative amplitudes of a pulse included in the pulse signal of the heart in a time domain and analyzes the center frequency using the time difference, wherein when the time difference is smaller than a time difference threshold value corresponding to the center frequency threshold value, the processing unit determines a period of the pulse signal of the heart having the time difference as a contraction period of the heart, and wherein when the time difference is greater than the time difference threshold value, the processing unit determines a period of the pulse signal of the heart having the time difference as a distension period of the heart.

11. The bio signal measuring apparatus of claim 8, wherein the processing unit compares center frequencies before and after the pulse signal penetrates the heart of the person to be measured, to calculate a variation in the center frequency, wherein when the variation in the center frequency is smaller than a center frequency variation threshold value, the processing unit determines a period of the pulse signal of the heart having the variation as a contraction period of the heart, and wherein when the variation in the center frequency is greater than the center frequency variation threshold value, the processing unit determines a period of the pulse signal of the heart having the variation as a distension period of the heart.

12. The bio signal measuring apparatus of claim 11, wherein the processing unit measures a time difference between positive and negative amplitude portions of a pulse included in the pulse signal of the heart in a time domain, compares a time difference before the pulse signal penetrates the person to be measured with a time difference after the pulse signal penetrates the person to be measured to calculate a variation in the time difference, and analyzes a variation in the center frequency using a variation in the time difference, wherein when the variation in the time difference is smaller than a time difference variation threshold value corresponding to the center frequency variation threshold value, the processing unit determines a period of the pulse signal of the heart having the variation as a contraction period of the heart, and wherein when the variation in the time difference is greater than the time difference variation threshold value, the processing unit determines a period of the pulse signal of the heart having the variation as a distension period of the heart.

13. The bio signal measuring apparatus of claim 8, wherein the processing unit calculates an amplitude of the pulse signal of the heart, wherein when the amplitude is greater than an amplitude threshold value, the processing unit determines a period of the pulse signal of the heart having the amplitude as a contraction period of the heart, and wherein when the amplitude is smaller than the amplitude threshold value, the processing unit determines a period of the pulse signal of the heart having the amplitude as a distension period of the heart.

14. The bio signal measuring apparatus of claim 8, wherein the processing unit compares amplitudes before and after the pulse signal penetrates the heart of the person to be measured, to calculate a variation in the amplitude, wherein when the variation in the amplitude is smaller than an amplitude variation threshold value, the processing unit determines a period of the pulse signal of the heart having the variation as a contraction period of the heart, and wherein when the variation in the amplitude is smaller than the amplitude variation threshold value, the processing unit determines a period of the pulse signal of the heart having the variation as a distension period of the heart.

15. The bio signal measuring apparatus of claim 1, wherein the processing unit converts the pulse signal of the heart from a time domain to a frequency domain to measure a bandwidth of the pulse signal of the heart in the frequency domain.

16. The bio signal measuring apparatus of claim 1, wherein the processing unit measures a duration of a pulse included in the pulse signal of the heart in a time domain and analyzes the bandwidth using the duration, wherein when the duration is shorter than a duration threshold value corresponding to the bandwidth threshold value, the processing unit determines a period of the pulse signal of the heart having the duration as a contraction period of the heart, and wherein when the duration is longer than the duration threshold value, the processing unit determines a period of the pulse signal of the heart having the duration as a distension period of the heart.

17. The bio signal measuring apparatus of claim 1, further comprising a transmitter configured to generate the pulse signal and transmit the pulse signal to the person.

18. The bio signal measuring apparatus of claim 1, wherein the processing unit detects the pulse signal of the heart of the person from the received pulse signal and removes a signal penetrating the person other than the heart of the person among the received pulse signal.

* * * * *